US008871281B2

(12) United States Patent
Miller

(10) Patent No.: US 8,871,281 B2
(45) Date of Patent: Oct. 28, 2014

(54) TREATMENT OF ORAL PHARYNGEAL DYSPHAGIA

(75) Inventor: Kevin Burke Miller, Minneapolis, MN (US)

(73) Assignee: Nestec S.A., Vevey (CH)

( * ) Notice: Subject to any disclaimer, the term of this patent is extended or adjusted under 35 U.S.C. 154(b) by 315 days.

(21) Appl. No.: 12/743,363

(22) PCT Filed: Oct. 7, 2008

(86) PCT No.: PCT/US2008/079044
§ 371 (c)(1),
(2), (4) Date: Aug. 17, 2010

(87) PCT Pub. No.: WO2009/067296
PCT Pub. Date: May 28, 2009

(65) Prior Publication Data
US 2011/0028382 A1    Feb. 3, 2011

Related U.S. Application Data

(60) Provisional application No. 60/988,930, filed on Nov. 19, 2007, provisional application No. 61/022,899, filed on Jan. 23, 2008.

(51) Int. Cl.
A61K 36/81     (2006.01)
A61K 47/00     (2006.01)
A61K 31/165    (2006.01)
A61K 31/164    (2006.01)
A23L 1/30      (2006.01)
A61K 45/06     (2006.01)
A23L 2/52      (2006.01)
A61K 31/357    (2006.01)

(52) U.S. Cl.
CPC ............ *A61K 31/165* (2013.01); *A61K 31/164* (2013.01); *A23L 1/30* (2013.01); *A23L 1/3002* (2013.01); *A61K 45/06* (2013.01); *A23L 2/52* (2013.01); *A61K 31/357* (2013.01)
USPC ......................................... 424/760; 424/439

(58) Field of Classification Search
USPC .................................................. 514/1.1, 23
See application file for complete search history.

(56) References Cited

U.S. PATENT DOCUMENTS

2003/0082249 A1* 5/2003 Gordon .......................... 424/760
2004/0197456 A1* 10/2004 Holahan ......................... 426/573
2004/0204486 A1* 10/2004 Hogestatt et al. .............. 514/549
2007/0190209 A1* 8/2007 Sinnott ............................. 426/72

FOREIGN PATENT DOCUMENTS

| AU | 2008326640 B2 | 8/2012 |
| EP | 1069105 | 1/2001 |
| JP | 07274915 | 10/1995 |
| JP | 2007151736 | 6/2007 |
| WO | 2004024154 | 3/2004 |
| WO | WO 2004/058301 | 7/2004 |
| WO | 2004069179 | 8/2004 |
| WO | 2006/086764 | 8/2006 |

OTHER PUBLICATIONS

Ebihara et al. 2005, J. American Geriatr Soc, 53:824-828, 2005.*
Avery-Smith et al. 1994, The American Journal of Occupational Therapy, 48: 235-239, 1994.*
Martin et al. 1991, Dysphagia, 6: 129-134, 1991.*
Iwasaki et al 1999, Phytomedicine, 6: 103-106, 1999.*
Ebihara et al, Combined Substance Used for Improving Deglutition Disorders, CN 1511542, Human Translation, 2004, pp. 1-12.*
Ebihara, Takae et al., "Capsaicin troche for swallowing dysfunction in older people," Journal of the American Geriatrics Society, vol. 53, No. 5, May 2005, pp. 824-828.
Smithard D.G., "Substance P and swallowing after stroke," Therapy Mar. 2006 GB, vol. 3, No. 2, Mar. 2006, pp. 291-298.
Ebihara, Takae et al., "Capsaicin and swallowing reflex," The Lancet, vol. 341, Jan. 1992, pp. 432.
Sasaki, H. et al., "New strategies for aspiration pneumonia," Internal Medicine (Tokyo, Japan), vol. 36, No. 12, Dec. 1997, pp. 851-855.
International Search Report received in corresponding PCT Application No. PCT/US2008/079044 filed Oct. 7, 2008.
Szallasi et al. "Vanilloid (Capsaicin) Receptors and Mechanisms" Pharmacological Reviews, vol. 51, No. 2, pp. 159-212, Copyright 1999, retrieved online on May 20, 2014.
Indian Office Action for Indian Application No. 3369/DELNP/2010 dated Apr. 30, 2014 (2 pages).
Rofes et al. "Pharmacological treatment of oropharyngeal dysphagia through TRPV1 stimulation" Department of Surgery, Hospital de Mataro, Catalonia, Spain, 9 pages.
Rofes et al. "Natural capsaicinoids improve swallow response in older patients with oropharyngeal dysphagia" Gut, 2012, 8 pages.
Garces-Claver et al. "Determination of Capsaicin and Dihydrocapsaicin in Capsicum Fruits by Liquid Chromatography-Electrospray/Time-of-Flight Mass Spectrometry" Journal of Agricultural and Food Chemistry, 2006, vol. 54, pp. 9303-9311.
Lida T. et al. "TRPV1 activation and induction of nociceptive response by a non-pungent capsaicin-like compound, capsiate" Neuropharmacology, 2003, vol. 44 (Abstract) (1 page).
Clave "Diagnosis and Management of Oropharyngeal Dysphagia in the Elderly" Nutrition and the Older Person, Dec. 2007, 13 pages.
Haramizu et al. "Capsiate, a Nonpungent Capsaicin Analog, Increases Endurance Swimming Capacity of Mice by Stimulation of Vanilloid Receptors" Biosci. Biotechnol. Biochem., 2006, vol. 70, pp. 774-781.

(Continued)

*Primary Examiner* — Blessing M Fubara
*Assistant Examiner* — Jennifer A Berrios
(74) *Attorney, Agent, or Firm* — K&L Gates LLP

(57) ABSTRACT

The invention provides compounds for use in a method of treating oral pharyngeal dysphagia in an individual and related products. One embodiment of the invention comprises administering to an individual an effective amount of a vanilloid receptor 1 (VR-1) agonist or high-affinity partial agonist to promote a swallow reflex.

19 Claims, No Drawings

(56) References Cited

OTHER PUBLICATIONS

Kawada et al. "In vivo and in vitro metabolism of dihydrocapsaicin, a pungent principle of hot pepper, in rats" Agricultural and Biological Chemistry, 1985, vol. 49 (Abstract) (1 page).

Yamasaki et al. "Cough reflex and oral chemesthesis induced by capsaicin and capsiate in healthy never-smokers" Cough, 2007, vol. 3, 7 pages.

Messeguer et al. "Physiology and Pharmacology of the Vanilloid Receptor" Current Neuropharmacology, 2006, vol. 4, pp. 1-15.

Ohnuki et al. "Administration of Capsiate, a Non-Pungent Capsaicin Analog, Promotes Energy Metabolism and Suppresses Body Fat Accumulation in Mice" Biosci. Biotechnol. Biochem, 2001, vol. 65, pp. 2735-2740.

Pelletier "Chemosenses, Aging, and Oropharyngeal Dysphagia, A Review" Topics in Geriatric Rehabilitation, vol. 23, No. 3, pp. 249-268, 2007.

* cited by examiner

TREATMENT OF ORAL PHARYNGEAL DYSPHAGIA

This application is a 371 of PCT/US2008/079044, filed on Oct. 7, 2008, which claims the benefit of U.S. Provisional Application No. 60/988,930, filed on Nov. 19, 2007, and of U.S. Provisional Application No. 61/022,899, filed on Jan. 23, 2008.

BACKGROUND OF THE INVENTION

1. Technical Field

The invention relates generally to the treatment of oral pharyngeal dysphagia, and, more particularly, to the use of vanilloid receptor 1 (VR-1) agonists to stimulate swallowing in an individual suffering from oral pharyngeal dysphagia.

2. Background Art

Dysphagia is a condition typified by a decreased ability to swallow. The normal swallow involves three distinct phases which are interdependent and well coordinated, they include: the oral, the pharyngeal, and the esophageal phases. In the oral phase, which is under voluntary control, food that has been chewed and mixed with saliva is formed into a bolus for delivery by voluntary tongue movements to the back of the mouth, into the pharynx. The pharyngeal phase is involuntary and is triggered by food/liquid bolus passing through the faucial pillars into the pharynx. Contraction of the three constrictors of the pharynx propel the bolus towards the upper oesophageal sphincter. Simultaneously, the soft palate closes the nasopharynx. The larynx moves upwards to prevent food or liquid passing into the airway, which is aided by the backward tilt of the epiglottis and closure of the vocal folds. The oesophageal phase is also involuntary and starts with the relaxation of the upper oesophageal sphincter followed by peristalsis, which pushes the bolus down to the stomach.

Esophageal dysphagia affects a large number of individuals of all ages, but is generally treatable with medications and is considered a less serious form of dysphagia. Oral pharyngeal dysphagia, on the other hand, is a very serious condition and is generally not treatable with medication. Oral pharyngeal dysphagia also affects individuals of all ages, but is more prevalent in older individuals. Worldwide, oral pharyngeal dysphagia affects approximately 22 million people over the age of 50.

The consequences of untreated or poorly managed oral pharyngeal dysphagia can be severe, including dehydration, malnutrition, airway obstruction with solid foods (choking), and airway aspiration of liquids and semi-solid foods, promoting aspiration pneumonia and/or pneumonitis. Severe oral pharyngeal dysphagia may require nutrition to be supplied by tube feeding. Mild to moderate oral pharyngeal dysphagia requires the texture of foods to be modified in order to minimize the likelihood of choking or aspiration. This may include the thickening of liquids and/or pureeing of solid foods, both of which have been shown to be the most effective means of preventing choking and aspiration during the eating process. Thickened liquids are designed to have three properties: (1) a more cohesive bolus that can be maintained throughout the action of swallowing, (2) slower delivery to the throat, thereby compensating for the increased period in which the swallowing reflexes prepare for the thickened liquid, and (3) provide greater density to increase awareness of the presence of food or liquid bolus in the mouth.

Oral pharyngeal dysphagia is often a consequence of an acute event, such as a stroke, brain injury, or surgery for oral or throat cancer. In addition, radiotherapy and chemotherapy may weaken the muscles and degrade the nerves associated with the physiology and nervous innervation of the swallow reflex. It is also common for individuals with progressive neuromuscular diseases, such as Parkinson's Disease, to experience increasing difficulty in swallow initiation. Representative causes of oropharyngeal dysphagia include those associated neurological illnesses (brainstem tumors, head trauma, stroke, cerebral palsy, Guillain-Barre syndrome, Huntington's disease, multiple sclerosis, polio, post-polio syndrome, Tardive dyskinesia, metabolic encephalopathies, amyotrophic lateral sclerosis, Parkinson's disease, dementia), infectious illnesses (diphtheria, botulism, Lyme disease, syphilis, mucositis [herpetic, cytomegalovirus, candida, etc.], autoimmune illnesses (lupus, scleroderma, Sjogren's syndrome), metabolic illnesses (amyloidosis, cushing's syndrome, thyrotoxicosis, Wilson's disease), myopathic illnesses (connective tissue disease, dermatomyositis, myasthenia gravis, myotonic dystrophy, oculopharyngeal dystrophy, polymyositis, sarcoidosis, paraneoplastic syndromes, inflammatory myopathy), Iatrogenic illnesses (medication side effects [e.g., chemotherapy, neuroleptics, etc.], post surgical muscular or neurogenic, radiation therapy, corrosive [pill injury, intentional]), and structural illnesses (cricopharyngeal bar, Zenker's diverticulum, cervical webs, oropharyngeal tumors, osteophytes and skeletal abnormalities, congenital [cleft palate, diverticulae, pouches, etc.]).

Improving an individual's ability and efficiency to swallow improves the individual's safety through reduced risk of pulmonary aspiration. An efficient swallow may permit greater independence from feeding assistance and/or reduced length of time spent in feeding-assistance during meal consumption. Efficient swallow also reduces the viscosity of liquids required for safety (e.g., pudding, honey and nectar thickness products) and may also limit the use of texture-modified foods. All of these previously described factors are aimed at improving an individual's quality of life. Ebihara et al. describe a method of improving upper respiratory reflexes, including coughing and swallowing, upon the oral administration of a capsaicin troche with each meal. Capsaicin Troche for Swallowing Dysfunction in Older People, *J. Am. Geriatrics Society*, 53(5):824-(2005).

Capsaicin (8-methyl-N-vanillyl-6-nonenamide) is a crystalline alkaloid found naturally in chili peppers and which may also be synthesized. Capsaicin is a vanilloid, capable of binding to and agonizing the vanilloid receptor 1 (VR-1). The VR-1 receptor is a transducers of nociceptive signals including heat and capsaicin. As noted above, oral administration of capsaicin has been shown to promote a swallow reflex. However, capsaicin is a particularly pungent and toxic compound. Physiological effects associated with oral administration of capsaicin include a burning sensation of heat from the mid-tongue to the throat, shortness of breath, fainting, nausea, and spontaneous vomiting. As a result, only small quantities of capsaicin may be administered without causing discomfort to the individual. In addition, methods such as that of Ebihara et al. require the administration of a troche prior to any food consumed by the individual and as a result of poor oral motor skills (ability to control the tongue) this method may introduce an additional risk of choking on the troche itself.

To this extent, a need exists for a method of treating oral pharyngeal dysphagia that does not suffer from the defects of known methods.

SUMMARY OF THE INVENTION

The invention provides a method of treating oral pharyngeal dysphagia in an individual and also an individual at risk of developing the sequelae of dysphagia- and related products. One embodiment of the invention comprises administering to an individual an effective amount of a vanilloid receptor 1 (VR-1) agonist or high-affinity partial agonist to promote a swallow reflex.

A first aspect of the invention provides a method for treating oral pharyngeal dysphagia in an individual, the method comprising: administering to the individual an effective amount of at least one vanilloid receptor 1 (VR-1) agonist, wherein the at least one VR-1 agonist promotes a swallow reflex in the individual.

A second aspect of the invention provides a method for promoting a swallow reflex in an individual, the method comprising: administering to the individual an effective amount of at least one vanilloid receptor 1 (VR-1) agonist.

A third aspect of the invention provides an orally-administrable liquid nutritional product comprising: at least one vanilloid receptor 1 (VR-1) agonist capable of promoting a swallow reflex in an individual.

A fourth aspect of the invention provides an orally-administrable liquid hydration product comprising: at least one vanilloid receptor 1 (VR-1) agonist capable of promoting a swallow reflex in an individual.

A fifth aspect of the invention provides a texture-modified food comprising: at least one vanilloid receptor 1 (VR-1) agonist capable of promoting a swallow reflex in an individual.

The illustrative aspects of the present invention are designed to solve the problems herein described and other problems not discussed, which are discoverable by a skilled artisan.

DETAILED DESCRIPTION

As indicated above, the invention provides a method of treating oral pharyngeal dysphagia in an individual and, more particularly, a method of promoting a swallow reflex comprising administering to the individual an effective amount of at least one vanilloid receptor 1 (VR-1) agonist.

The extract of peppers has been described as pungent which means a sharp or biting sensation when describing a food. Capsaicin and its analogues are classed as vanilloids because of the vanillin-related monomethylated orthodiphenolic moiety on the amide end of these molecules. Many molecules with analogous physiologic effects share this structural characteristic with capsaicin. The capsinoids found in the extract of hot chili include: capsaicin (69%), dihydrocapsaicin (22%), as well as three fairly minor compounds nordihydrocapsaicin (7%), homocapsaicin (1%), and homodihydrocapsaicin (1%). There are other analogs of capsaicin that have been extracted from chili peppers including Capsiate and the other minor compounds (e.g., dihydrocapsiate, etc).

As used herein, the terms "non-pungent" refer to vanilloid receptor agonists that elicit a minimal or no: sharp or biting sensation or sensation of heat. Capsiate has been extracted from a non-pungent cultivar of red pepper, CH-19 sweet, and shown to be a capsaicin analogue called capsinoid that has an ester bond instead of the amide bond between the vanillyl moiety and fatty acid chain.

The biologic effects of the capsicum family compounds rely on their interaction with various neural receptors. The hot sensation from eating chilies is caused by the interaction of the capsaicin with the vanilloid-receptor 1 (Nociceptors surrounding the taste sensors of the mouth). The receptors are defined as being sensitive to stimulus by a noxious substance. Capsaicin, and the related compounds, is a vanilloid receptor agonist which selectively activates the Nociceptors. Some of these nociceptors are thermal sensors, so there is a sensation of heat. The non-pungent aspect of capsiate has not been fully elucidated, but it appears that the structural differences between capsiate and capsaicin are adequate to prevent the sensation of heat, despite activating the vanilloid receptors (TRPV1).

As used herein, the terms "treatment," "treating," and "treat" refer to both prophylactic or preventive treatment and curative or disease-modifying treatment, including treatment of patients at risk of contracting a disease or suspected to have contracted a disease, as well as patients who are ill or have been diagnosed as suffering from a disease or medical condition. The terms "treatment" and "treat" also refer to the maintenance and/or promotion of health in an individual not suffering from a disease but who may be susceptible to the development of an unhealthy condition, such as oral pharyngeal dysphagia. Consequently, an "effective amount" is an amount that treats a disease or medical condition in an individual or, more generally, provides a nutritional, physiological, or medical benefit to the individual.

VR-1 agonists other than capsaicin promote a swallow reflex similar to capsaicin. In addition to capsaicin, VR-1 agonists include capsiate, dihydrocapsaicin, dihydrocapsiate, nordihydrocapsaicin, nordihydrocapsiate, homocapsaicin, homodihydrocapsaicin, vanillylamide of n-nonanoic acid (VNA), anandamide, resiniferatoxin, and olvanil. However, while promoting a swallow reflex similar to capsaicin, these VR-1 agonists are less pungent and less toxic than capsaicin. Accordingly, such compounds may be administered at higher concentrations without inducing the unpleasant affects associated with capsaicin. As will be recognized by one having ordinary skill in the art, pharmaceutically acceptable derivatives of capsaicin and the other VR-1 agonists above may similarly be employed in accordance with the invention.

One method according to the invention comprises administering to an individual an effective amount of at least one VR-1 agonist or a pharmaceutically acceptable derivative thereof, wherein the at least one VR-1 agonist promotes a swallow reflex. Such a method is preferably employed in the treatment of oral pharyngeal dysphagia in the individual.

The oral pharyngeal dysphagia may be a consequence of at least one of surgery for oral cancer, surgery for throat cancer, a stroke, a brain injury, and a progressive neuromuscular disease, such as Parkinson's Disease.

In a preferred embodiment, one or more VR-1 agonists are administered in a nutritional supplement, such as a nutrient-dense beverage. In another preferred embodiment, one or more VR-1 agonists are administered in a hydration supplement. Such supplements may be in the form of a thickened liquid. In yet another preferred embodiment, one or more VR-1 agonists are administered in a texture-modified food.

Most VR-1 agonists, including capsaicin, are only slightly soluble in water, but quite soluble in alcohols, fats, and oils. Accordingly, orally-administrable nutritional or hydrating products according to the invention preferably include an alcohol, fat, or oil in which the VR-1 agonist may be dissolved. Orally-administrable nutritional products of the invention may further contain any number of ingredients that provide a nutritional, physiological, or medical benefit to an individual. Such ingredients include, for example, proteins, soluble and/or insoluble fibers, fatty acids, vitamins, minerals, sugars and/or other carbohydrates, flavor agents, thickening agents (e.g., starches, gums, and/or cellulose), and medicaments or other therapeutic agents.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

I claim:

1. A method for treating oral pharyngeal dysphagia in an individual in need thereof, the method comprising: administering to the individual an effective amount of a product comprising vanilloid receptor 1 (VR-1) agonists capable of promoting a swallow reflex in the individual, the product further comprising a thickening agent, wherein the VR-1 agonist comprises capsaicin and an additional VR-1 agonist selected from the group consisting of capsiate, dihydrocapsiate, nordihydrocapsiate, anandamide and combinations thereof.

2. The method of claim 1, wherein the thickening agent comprises starch.

3. The method of claim 1, wherein the individual is suffering from oral pharyngeal dysphagia as a consequence of at least one of the following: cancer chemotherapy, cancer radiotherapy, surgery for oral cancer, surgery for throat cancer, a stroke, a brain injury, and a progressive neuromuscular disease.

4. The method of claim 3, wherein the progressive neuromuscular disease is Parkinson's Disease.

5. The method of claim 1, wherein the VR-1 agonists are administered in a non-hydrating beverage.

6. The method of claim 5, wherein said nonhydrating beverage is a caffeinated beverage.

7. The method of claim 1, wherein the product is a thickened beverage, the thickening agent selected from the group consisting of starches, gums, cellulose and combinations thereof.

8. The method of claim 1, wherein said product is a coffee or carbonated beverage.

9. The method of claim 1, wherein said product is an alcoholic beverage or non-alcoholic simulated beverage.

10. The method of claim 1, wherein the product is a soup.

11. The method of claim 1, wherein the product is a yogurt.

12. The method of claim 1, wherein the product is an ice cream.

13. The method of claim 1, wherein the product is a medicinal product.

14. The method of claim 13, wherein the medicinal product is a pharmaceutical.

15. The method of claim 13, wherein the medicinal product is a nutraceutical.

16. The method of claim 1, wherein the product is a nutritional supplement.

17. The method of claim 1, wherein the product is an herbal preparation.

18. The method of claim 1 wherein the product is a vitamin, mineral or vitamin and mineral supplement.

19. The method of claim 1 wherein the product comprises an ingredient in which the VR-1 agonists are dissolved and which is selected from the group consisting of alcohol, fat and oil.

* * * * *